United States Patent [19]

Schwartz

[11] Patent Number: 4,636,215
[45] Date of Patent: Jan. 13, 1987

[54] COMBINATION TRAY AND CONDYLAR PROSTHESIS FOR MANDIBULAR RECONSTRUCTION AND THE LIKE

[75] Inventor: Harry C. Schwartz, Granada Hills, Calif.

[73] Assignee: REI, Inc., Torrance, Calif.

[21] Appl. No.: 569,912

[22] Filed: Jan. 11, 1984

[51] Int. Cl.$^4$ ............................................. A61F 2/28
[52] U.S. Cl. ...................................... 623/16; 623/66; 128/92 R
[58] Field of Search ................... 3/1; 128/92 R, 92 C; 433/173, 174, 175, 176; 623/16

[56] References Cited

U.S. PATENT DOCUMENTS

| | | | |
|---|---|---|---|
| 3,488,779 | 1/1970 | Christensen | 623/16 X |
| 3,683,422 | 8/1972 | Stemmer et al. | 128/92 CX |
| 3,720,959 | 3/1973 | Hahn | 623/16 |
| 3,849,805 | 11/1974 | Leake et al. | 128/92 CX |
| 4,172,128 | 10/1979 | Thiele et al. | 623/16 X |
| 4,455,256 | 6/1984 | Urist | 623/16 X |
| 4,472,840 | 9/1984 | Jefferies | 623/16 |

Primary Examiner—Richard J. Apley
Assistant Examiner—Alan W. Cannon
Attorney, Agent, or Firm—Drucker & Sommers

[57] ABSTRACT

The invention comprises a urethane-coated polyethylene terephthalate mesh bone induction tray, with a simulated condyle integrally affixed to the mesh tray without the use of metal pins, screws and the like. The invention lies in the integral affixing of a urethane plastic, e.g. polyether urethane simulated condyle to the end portion of a plastic mesh tray. The simulated condyle may be customized, i.e., premeasured for a particular patient before the operation, or may be custom-contoured from one of several pre-formed condyle/tray combinations having varying shapes or geometries. The condyle portion is further preferably reinforced with a core of stainless steel wire, e.g., a Kirschner rod or wire, running the length of the condyle portion and projecting beyond, into the tray, to permit embedding of the wire into the remaining osseous structure, thus anchoring the entire combination.

17 Claims, 5 Drawing Figures

COMBINATION TRAY AND CONDYLAR PROSTHESIS FOR MANDIBULAR RECONSTRUCTION AND THE LIKE

BACKGROUND OF THE INVENTION

Surgical reconstruction of bone defects resulting from resection, severe trauma, or congenital defects has become increasingly common. Reconstructive techniques have involved the use of solid bone grafts. However, solid bone grafts may require extensive surgery, are difficult to contour, and are subject to stress fractures.

Another technique involves osteogenesis with fresh cancellous bone chips and marrow as an amorphous particulate graft. Because successful particulate bone grafting depends on adequate stability, metal trays (titanium chrome cobalt alloys, or stainless steel mesh) have been used to provide fixation and form for the particles. Metal trays are somewhat unsatisfactory, however, as they cannot be readily adapted to achieve optimum fit or contour at the operating table.

For osseous reconstructions which include replacing a condyle, using a metallic bone induction tray, a metallic simulated condyle is affixed to the tray by screws or pins or wire. This usage is subject to the disadvantages of metal fatigue, difficulty of contour modification, and separation of the condyle from the tray proper.

In order to obviate some of the difficulties encountered in the use of metal trays, Leake et al, in 1972, developed an implant tray fabricated of Dacron ®[1] and a urethane plastic, e.g., polyether urethane (U.S. Pat. No. 3,849,805, issued Nov. 26, 1974). This non-metallic tray can be fabricated very easily and in a variety of configurations, is very flexible and can be easily altered at the operating table with scissors or scalpel. The flexibility and ease of use of this non-metallic tray indicate its preferability over metal trays.

[1]Dacron is a registered trademark of E. I. DuPont de Nemours for its brand of polyethylene terephthalate.

The Leake tray, however, is not conveniently utilized for reconstruction when the bone to be reconstructed is needed for articulation, and the condyle of the patient is not available due to severe trauma, terminal resection or congenital defect. Previously, with osseous reconstruction including the condyle using the Leake tray, a strut of solid bone has been placed in the trough and fixed in place by metal pins or screws, and serves as a condyle. The use of solid bone for this purpose has the same disadvantages as the use of any other solid bone graft, i.e., irregular remodelling, difficulty in contouring, and subjectivity to stress fractures. inadequate, the need for a novel device which would permit the condyle to be reconstructed following a terminal resection has long existed.

As will be seen, the proposed invention has numerous advantages over the bone induction/condylar reconstruction trays used in the past. The device is a prosthetic condyle, formed from a biocompatible plastic, which is integrally affixed to a non-metallic bone induction tray. This device eliminates the need to use any solid bone grafts or metallic prostheses in the reconstructive process. Additionally, fabrication on standard molds may be readily carried out, with contouring and customizing of the tray/condyle combination readily accomplished at the operating table. The invention expands the use of existing non-metallic bone induction trays where the patient's condyle is not available or not usable.

SUMMARY OF THE INVENTION

The invention comprises a urethane-coated Dacron ® mesh bone induction tray, with a simulated condyle integrally affixed to the mesh tray without the use of metal pins, screws and the like. The invention lies in the integral affixing of a urethane plastic, e.g. polyether urethane simulated condyle to the end portion of a Dacron ®/Urethane mesh tray. The simulated condyle may be customized, i.e., premeasured for a particular patient before the operation, or may be custom-contoured from one of several pre-formed condyle/tray combinations having varying shapes or geometries. The condyle portion is further preferably reinforced with a core of stainless steel wire, e.g., a Kirschner rod or wire, running the length of the condyle portion and projecting beyond, into the tray, to permit embedding of the wire into the remaining osseous structure, thus anchoring the entire combination.

DETAILED DESCRIPTION OF THE INVENTION

Figure 1:
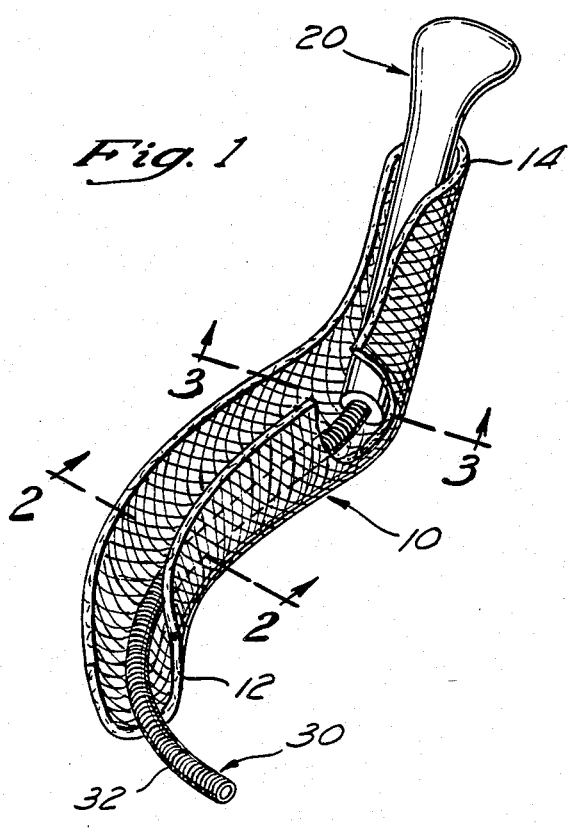
FIG. 1 is a side view of a typical mandibular tray with a single condyle extending from one end.
Figure 2:
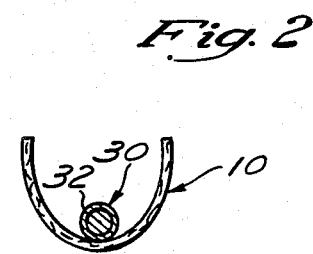
FIG. 2 is cross-section taken along 2—2 of FIG. 1.
Figure 3:
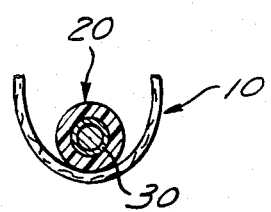
FIG. 3 is a cross-section taken along 3—3 of FIG. 1.
Figure 4:
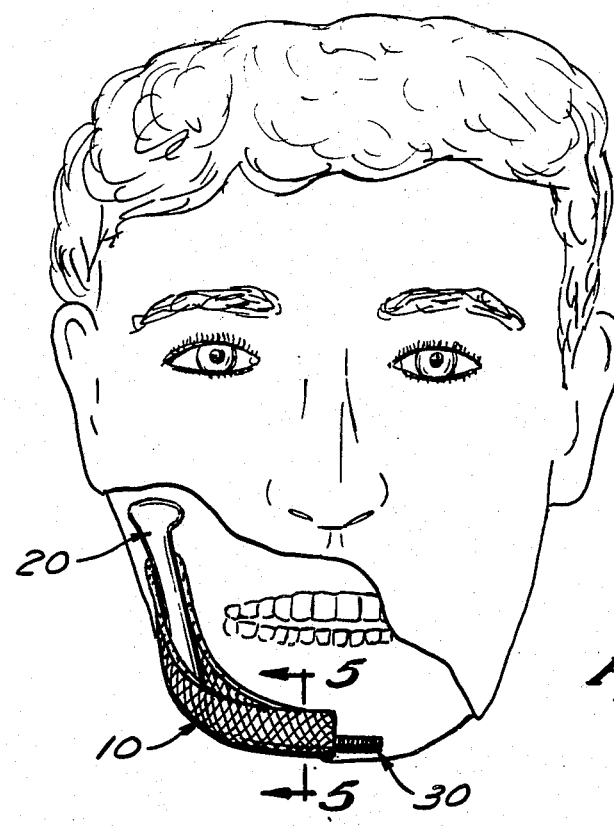
FIG. 4 is a front view showing the tray/condyle combination of this invention implanted in a human.

Referring to the drawings in this case, and particularly to FIG. 1, it may be seen that the invention is directed towards the combination of a non-metallic hollow mesh tray 10 particularly adaptable for mandibular reconstruction, and an integral, molded-in-place or otherwise integrally affixed non-metallic simulated condyle portion 20 at one (or both) ends of the hollow mesh tray.

The body 12 of the mandibular reconstruction tray 10 is simulative of the periphery of the body of a mandible, with its two opposing ends 14 simulative of the ascending ramii. While other plastic materials may be used in this manner, providing the characteristics of biocompatibility and relative inertness, adequate physical strength, appropriate rigidity and simple fabricating methods, the preferred embodiment is a tray 10 made of polyethylene terephthalate (Dacron ®) mesh impregnated with a polyether urethane elastomer.

The condylar end portion 20 is simulative of the condyloid process on the ramus of the mandible. While other plastic materials may be used for the molding of this part, especially medium viscosity casting liquids that are cured by elevated temperatures, the preferred embodiment utilizes polyether urethane elastomers. The mesh tray and the simulated condyle are integrally affixed with the condyle portion 20 inserted into the trough of the tray 10 and extending beyond the upper edge 14 of the tray. It is understood that for the purposes of the detailed description and the claims herein that "integrally affixed" encompasses the molding of the two members (10, 20) together as one unit, and also the affixing of the said two members (10, 20) with compatible adhesives without pins or screws or the like.

As seen in FIG. 1, it is presently preferred that there may be a reinforcing rod 30 molded into the simulated condyle 20. Preferably a stainless steel rod or wire—e.g. Kirshner wire—is used for reinforcing, although other well-tolerated reinforcing wire materials may be used. The reinforcing rod 30 runs generally the length of the condylar portion 20, or it may, preferably, extend beyond the end of the molded condyle portion into the bone-induction tray 10. It is contemplated that this reinforcing rod 30 may be used to anchor the tray end to any remaining osseous structure at the border of the osseus defect. While this reinforcing rod 30 may be of varying diameters, it is preferred that the rod have a serrated periphery 32 for enhanced anchoring of the rod to the remaining osseous structure.

The plastic mesh tray 10 is manufactured according to the method disclosed by Leake, U.S. Pat. No. 3,849,805. Preferably, a tray made of Dacron ® mesh is impregnated, i.e., coated with a polyether urethane elastomer. The mesh is saturated with the (catalyzed) urethane and the excess is removed by calendering between sheets of polyethylene. The impregnated mesh is then draped around a solid model of the section to be reconstructed and contoured tightly around the model with the use of small spring clamps, or wooden clothespins. The mesh structure is then cured in a circulating oven at about 200° F., for about six hours.

Preparation of the condylar portion 20 generally involves the selection of the appropriate size and shape of mold for the particular patient, and the casting of that mold with preferably polyether urethane elastomers, or other medium viscosity casting liquids. A reinforcing rod 30 is inserted into the mold carrying liquid elastomers, which is then allowed to polymerize by curing in a circulating oven at about 200° F.

The cured urethane-impregnated (or urethane-coated) Dacron ® mesh tray 10 is removed from the mold, and the molded condylar portion 20 is inserted into the end of the tray with the condyle portion extending beyond the edge of the tray for the appropriate distance as shown in FIG. 1.

Additional urethane is then applied around the contact points of the tray and the condylar portion 20 and allowed to polymerize, thus integrally affixing the two portions.

Following further curing at room temperature, the implant is trimmed to size. It is sterilized by antoclaving.

It is, of course, understood that this device also could be molded as a one piece unit using various casting methods without departing from the spirit of the invention.

It has been found that the non-metallic bone induction mesh tray combined as above with the simulated condyle has been well-tolerated on an experimental basis in humans. There have been no systemic effects observed, and local tissue response has been minimal. The combination is basically bio-compatible and may remain in situ for extended lengths of time or possibly permanently.

Figure 5:
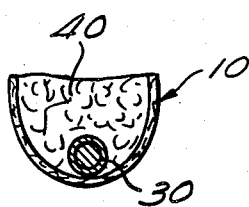
FIG. 5 is a cross-section taken along line 5—5 of FIG. 4.

The configuration of the bone formed by this induction method is guided by the contours of the implant tray. The cancellous bone chips and marrow 40 are packed in the implant tray 10 (see FIG. 5) so as to surround any reinforcing rod (30) which extends into the tray. Thus, as osteogenesis occurs, the reinforcing rod (30) is in the center of the new bone formed and truly integrates the new bone with the condylar portion (20).

This enhances the stress-bearing characteristics of the new bone as well as facilitating ease of articulation.

This novel combination is also adaptable for long bone reconstruction where the patient's condyle is unavailable or not usable, as well as for other osseous reconstruction where a condyle is needed.

The structures and methods set forth above are merely illustrative and may be varied or modified, or different forms or shapes could be used to produce the same desirable results without departing from the scope of the inventive concept.

I claim:

1. A device for reconstruction of bone, and for osteogenesis, employing cancellous bone chips and marrow, comprising:
   a flexible tray, made of a urethane coated plastic material, shaped approximately in the form of the bone to be reconstructed, adapted to hold said cancellous bone chips and marrow, and having openings allowing tissue ingrowth into all portions of the tray; and
   at least one plastic simulated condyle, integrally affixed to one end of said flexible tray.

2. The device, as in claim 1, wherein the plastic used for the simulated condyle is a urethane elastomer.

3. The device, as in claim 1, including a reinforcing rod generally extending within, and along the length of, said simulated condyle and said flexible tray.

4. The device, as in claim 3, wherein said reinforcing rod extends beyond said simulated condyle into said flexible tray.

5. The device, as in claim 3, wherein said reinforcing rod has a serrated periphery.

6. A device for reconstruction of bone, comprising:
   (a) a flexible tray, made of a urethane coated plastic material, shaped approximately in the form of the bone to be reconstructed; and
   (b) at least one simulated condyle, made of a plastic material, integrally affixed by compatible adhesives to the flexible tray.

7. A device for reconstruction of bone comprising:
   (a) a flexible tray, made of a urethane coated plastic material, shaped approximately in the form of the bone to be reconstructed; and
   (b) at least one simulated condyle, made of a plastic material, integrally affixed to the flexible tray by being molded, in place, to said flexible tray.

8. The device, as in claim 4, wherein the said reinforcing rod has a serrated periphery.

9. A device, as in claim 6, including a reinforcing rod generally extending within, and along the length of, said simulated condyle and said flexible tray.

10. The device, as in claim 9, wherein said reinforcing rod extends beyond said condyle into said flexible tray.

11. The device, as in claim 6 wherein the simulated condyle is integrally affixed by polyether urethane.

12. A device, as in claim 9, wherein said reinforcing rod has a serrated periphery.

13. A device, as in claim 7, including a reinforcing rod generally extending within, and along the length of said simulated condyle and said flexible tray.

14. A device, as in claim 13, wherein said reinforcing rod extends beyond said condyle into said flexible tray.

15. A device, as in claim 13, wherein said reinforcing rod has a serrated periphery.

16. A device, as in claim 7, wherein said simulated condyle is integrally affixed by polyether urethane.

17. The device, as in claim 3, wherein said reinforcing rod extends beyond said flexible tray.

* * * * *